(12) United States Patent
Christian

(10) Patent No.: US 8,597,288 B2
(45) Date of Patent: Dec. 3, 2013

(54) VACUUM-STABILIZED ABLATION SYSTEM

(75) Inventor: Steven C. Christian, New Brighton, MN (US)

(73) Assignee: St. Jude Medical, Artial Fibrillation Division, Inc., St. Paul, MN (US)

(*) Notice: Subject to any disclaimer, the term of this patent is extended or adjusted under 35 U.S.C. 154(b) by 856 days.

(21) Appl. No.: 12/408,632

(22) Filed: Mar. 20, 2009

(65) Prior Publication Data

US 2010/0081987 A1 Apr. 1, 2010

Related U.S. Application Data

(60) Provisional application No. 61/101,972, filed on Oct. 1, 2008.

(51) Int. Cl.
*A61B 18/18* (2006.01)

(52) U.S. Cl.
USPC .............. 606/41; 606/45; 606/46; 606/47; 606/48; 606/49; 606/50

(58) Field of Classification Search
USPC .............. 606/41, 45–50; 607/126; 604/20–22
See application file for complete search history.

(56) References Cited

U.S. PATENT DOCUMENTS

| | | | |
|---|---|---|---|
| 5,427,119 A | 6/1995 | Swartz et al. | |
| 5,497,774 A | 3/1996 | Swartz et al. | |
| 5,564,440 A | 10/1996 | Swartz et al. | |
| 5,571,088 A | 11/1996 | Lennox et al. | |
| 5,575,772 A | 11/1996 | Lennox | |
| 5,628,316 A | 5/1997 | Swartz et al. | |
| 5,640,955 A | 6/1997 | Ockuly | |
| 5,656,028 A | 8/1997 | Swartz et al. | |
| 5,690,611 A | 11/1997 | Swartz et al. | |
| 5,715,818 A | 2/1998 | Swartz et al. | |
| 5,860,974 A | 1/1999 | Abele | |
| 5,971,983 A | 10/1999 | Lesh | |
| 6,004,269 A | 12/1999 | Crowley et al. | |
| 6,238,393 B1 | 5/2001 | Mulier et al. | |
| 6,314,962 B1 | 11/2001 | Vaska et al. | |
| 6,314,963 B1 | 11/2001 | Vaska et al. | |
| 6,514,250 B1 * | 2/2003 | Jahns et al. | 606/41 |
| 6,689,128 B2 | 2/2004 | Sliwa, Jr. et al. | |
| 6,701,931 B2 | 3/2004 | Sliwa, Jr. et al. | |
| 6,802,840 B2 | 10/2004 | Chin et al. | |
| 6,837,887 B2 * | 1/2005 | Woloszko et al. | 606/41 |

(Continued)

OTHER PUBLICATIONS

Kiser, A. C., et al., "Evaluation of a Novel Epicardial Atrial Fibrillation Treatment System," The Annals of Thoracic Surgery, pp. 300-303, 2008.

(Continued)

*Primary Examiner* — Bhisma Mehta
*Assistant Examiner* — Larry R Wilson
(74) *Attorney, Agent, or Firm* — Wiley Rein LLP

(57) ABSTRACT

Cardiac ablation systems include vacuum-stabilized, irrigated ablation devices that have ablating elements capable of providing regions of relatively low pressure to maintain the ablating element in a stable position relative to the tissue, or minimize relative movement of the ablating element relative to the tissue. The ablation elements have integrated structures for vacuum-stabilization. The devices also include one or more electrodes for both orienting the ablating element as well as for diagnostic purposes.

21 Claims, 12 Drawing Sheets

(56) References Cited

U.S. PATENT DOCUMENTS

| | | |
|---|---|---|
| 6,858,026 B2 | 2/2005 | Sliwa, Jr. et al. |
| 7,052,493 B2 * | 5/2006 | Vaska et al. ............... 606/41 |
| 2004/0054369 A1 * | 3/2004 | Nelson et al. ............... 606/41 |
| 2004/0267086 A1 * | 12/2004 | Anstadt et al. ............... 600/17 |
| 2008/0045936 A1 | 2/2008 | Vaska et al. |
| 2010/0016786 A1 * | 1/2010 | Drews et al. ............... 604/22 |

OTHER PUBLICATIONS

Athanasiou, T., et al., "Expanded Use of Suction and Stabilization Devices in Cardiothoracic Surgery," The Society of Thoracic Surgeons, pp. 1126-1130, 2003.

* cited by examiner

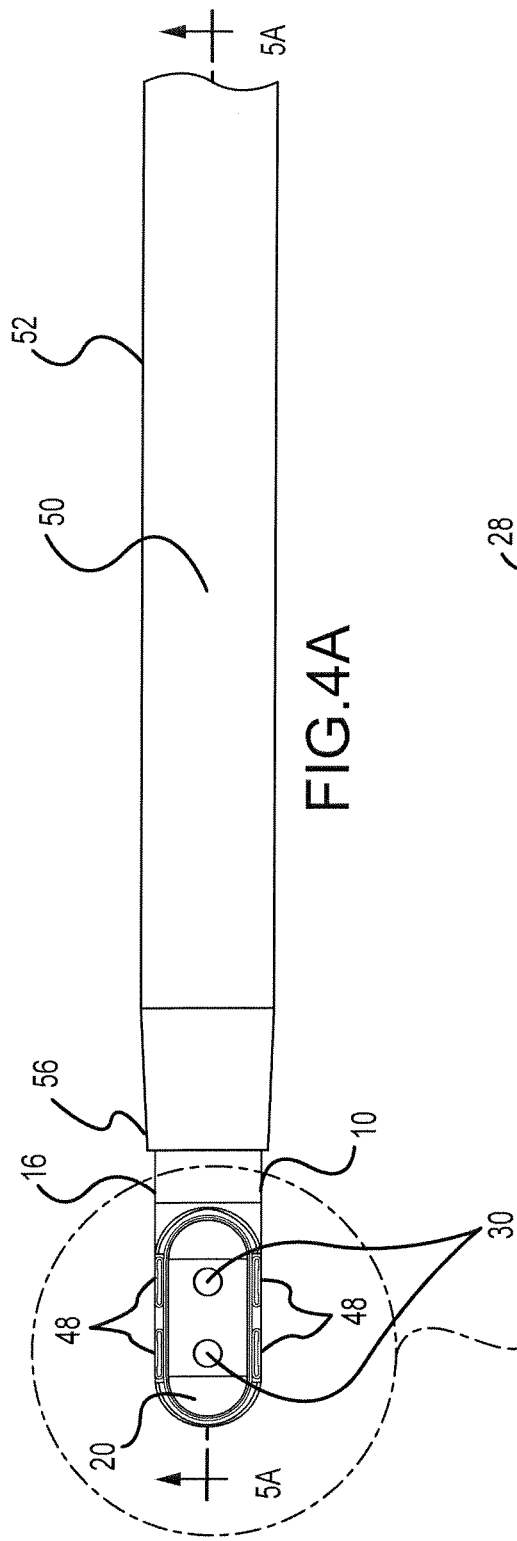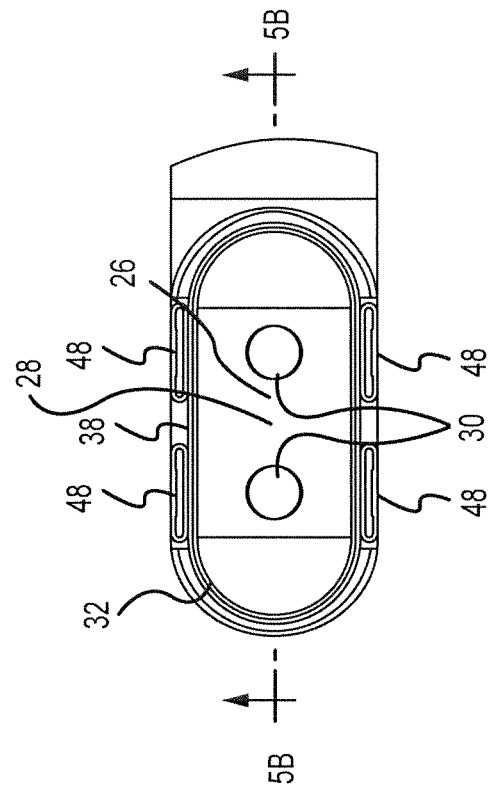

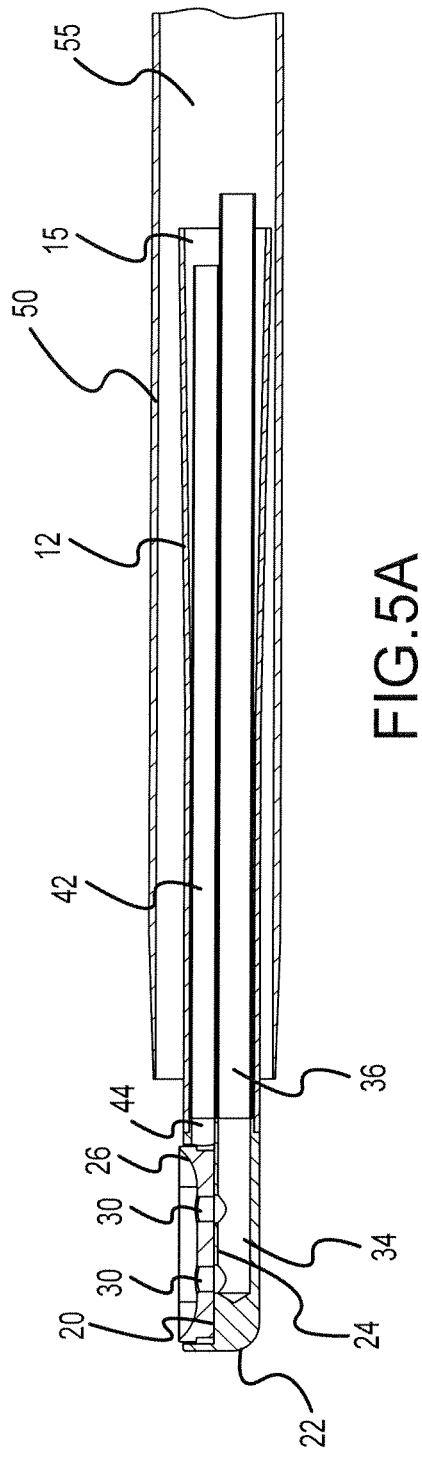
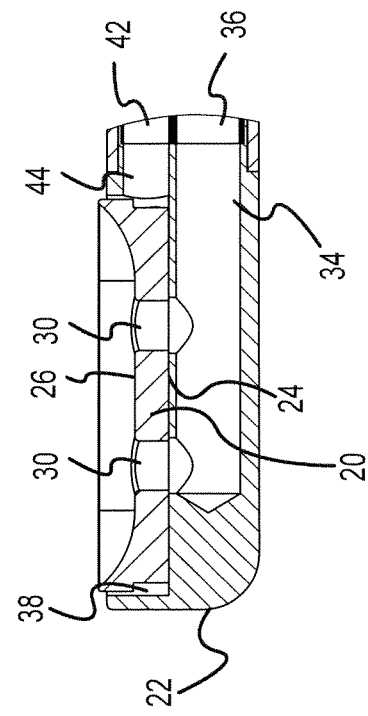
FIG.5A
FIG.5B

VACUUM-STABILIZED ABLATION SYSTEM

CROSS-REFERENCE TO RELATED APPLICATIONS

This application claims the benefit of U.S. provisional application No. 61/101,972, filed Oct. 1, 2008 ("the '972 application"). This application is related to U.S. application Ser. No. 11/785,427, filed 17 Apr. 2007 ("the '427 application"). The '972 and the '427 applications are both hereby incorporated by reference as though fully set forth herein.

BACKGROUND OF THE INVENTION a. Field of the Invention

The present disclosure pertains generally to an electrophysiological device and method for providing energy to biological tissue and, more particularly, to an ablation system that uses vacuum stabilization to provide greater contact between an ablation element and tissue.

b. Background Art

The heart beats or contracts when an electrical impulse originating from the sinoatrial node (SA node) travels through the right and left atria, and then activates the atrioventricular node (AV node). From the AV node, the electrical impulse travels through the right and left ventricles via a group of specialized fibers called the His-Purkinje fibers. The impulse causes synchronized contraction of the chambers of the heart. Cardiac conduction irregularities, or any change from the normal sequence of electrical impulses, can cause various arrythmias, such as atrial fibrillation, atrial flutter and certain ventricular arrhythmias. These conditions can decrease cardiac output and reduce tissue perfusion to the detriment of a subject.

Cardiac ablation is a procedure for treating various arrythmias by selectively damaging heart tissue in the region where aberrant or abnormal electrical activity is occurring. The damaged tissue blocks the aberrant pathways and restores normal heart rhythm. Various energy delivery schemes may be used, including, but not limited to, cryogenic ablation, radiofrequency (RF) ablation, laser ablation, ultrasound ablation, and microwave ablation. Ablation devices are used to create linear lesions or tiny scars that cut-off or disconnect the abnormal electrical pathway.

Ablation procedures rely on stable contact between the medical device and the cardiac tissue. For certain ablation procedures, such as a left atrial pulmonary vein isolation (PVI) procedure, the epicardial surfaces of posterior portions of a heart must be accessed. To reach such surfaces from an anterior location (e.g., via a minimally invasive subxiphoid incision) requires the catheter, in particular the distal portion of an elongate catheter, to traverse a tortuous route to reach target tissue. Establishing adequate contact with the target tissue to successfully perform a PVI (i.e., create a continuous lesion or set of connected lesions around one or more pulmonary veins) presents challenges to the practitioner. Furthermore, in some transvenous catheter applications, the point of electrode-tissue contact is as far as about 150 cm away from the point of application of force. In some catheter applications, the point of electrode-tissue contact is as far as about 150 cm away from the point of application of force. These challenges give rise to functional and theoretical challenges associated with conventional devices, and thus, the ability to accurately stabilize the device at the point of contact with a line of target tissue is increasingly important. Applying a vacuum at the point of contact has been contemplated for adhering the device to tissue.

There is a need for electrophysiological devices that provide greater contact stability for control of medical treatments.

There is a need for improved RF electrode ablation elements that provide greater stability, i.e., limit relative motion between the ablating element and the tissue at the point of contact.

BRIEF SUMMARY OF THE INVENTION

The systems and methods described herein are useful for the ablation of cardiac tissue for treating cardiac conduction irregularities that can cause various arrhythmias such as atrial fibrillation, atrial flutter and certain ventricular arrhythmias. In particular, the systems and methods described herein are useful for the ablation of epicardial tissue via a percutaneous subxiphoid approach. Disclosed herein are vacuum-stabilized, irrigated ablation devices that include ablating elements capable of providing regions of relatively low pressure to maintain the ablating element in a stable position relative to the tissue, or minimize relative movement of the ablating element relative to the tissue. The devices of the present invention also include one or more pairs of electrodes positioned on opposite sides of the ablating element for both orienting the ablating element as well as for diagnostic purposes. Also disclosed herein are methods of using the improved devices in cardiac ablation procedures.

An object of the present invention is to provide ablation systems having improved stability at the point of contact.

Another object of the present invention is to provide ablation systems incorporating ablating elements having integrated vacuum capture mechanisms.

A further object of the present invention is to provide ablation systems having directional ablating elements and means for orienting the ablating elements relative to a target tissue.

An ablation catheter as described herein includes an elongate body defining a lumen therethrough, a proximal end, a distal portion, and at least one ablating element coupled to the distal portion. The at least one ablating element includes a first surface and a second surface, and the second surface includes a base portion, at least one port and a rim. The ablation catheter further includes at least one cardiac electrode coupled to the distal portion of the elongate body, a suction lumen coupled to the at least one port at a distal end thereof and a source of varying pressure at a proximal end thereof. Additionally, the ablation catheter includes an irrigation channel surrounding at least a portion of the rim, and an irrigation lumen fluidly coupled to the irrigation channel at a distal end thereof and a source of irrigation fluid at a proximal end thereof. In one embodiment, the second surface has a concave shape and is adapted to be oriented opposite a target tissue.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 4A is a top view of a distal portion of an ablation system described herein.

FIG. 4B is an enlarged view of the ablation tip depicted in FIG. 4A.

FIG. 5A depicts a cross-sectional elevation view of the ablation system depicted in FIG. 4A taken along line A-A.

FIG. 5B is an enlarged cross-sectional elevation view of the ablation tip depicted in FIG. 5A.

DETAILED DESCRIPTION OF THE INVENTION

Described herein are tissue ablation systems useful, for example, in the treatment of cardiac conduction irregularities that can cause acute and chronic arrhythmias, such as atrial fibrillation, atrial flutter, and ventricular rhythm disorders. The systems and methods will be described in connection with epicardial tissue ablation utilizing radiofrequency (RF) electrodes; however, it is contemplated that the described features may be incorporated into or combined with other energy delivery schemes, as would be appreciated by one of ordinary skill in the art by virtue of the teachings herein.

Figure 1:
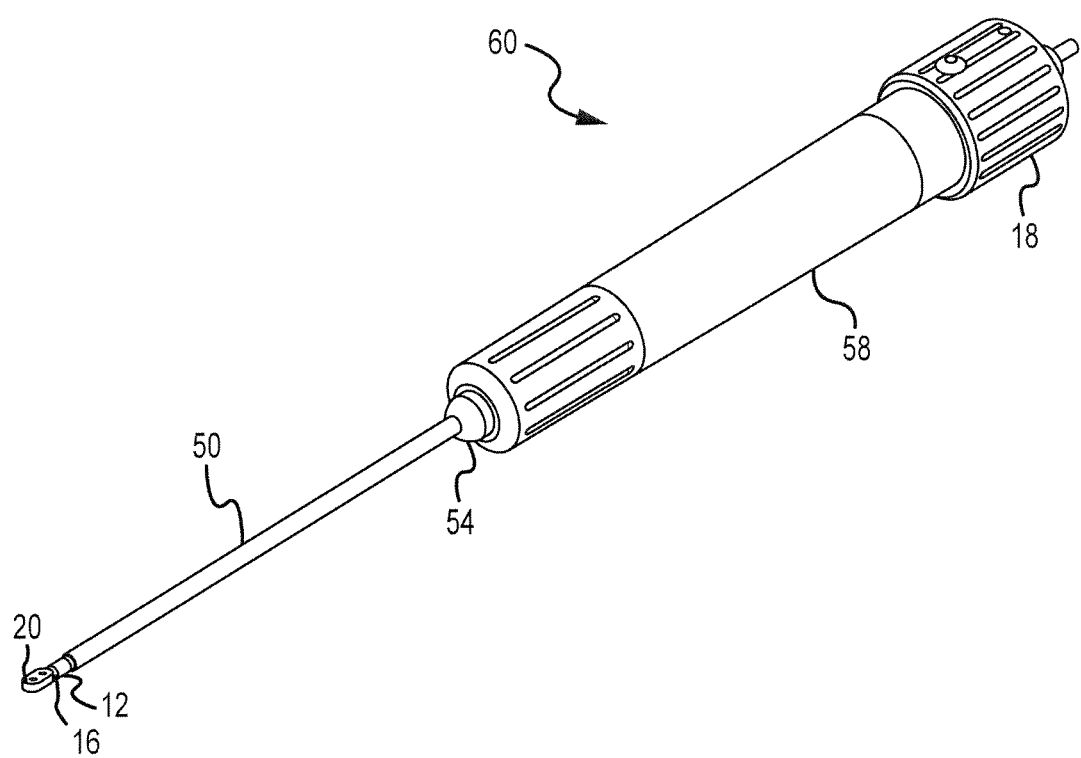
FIG. 1 is a perspective view of one embodiment of an ablation system according to the present invention.

With reference to FIG. 1, an ablation system 60 is shown. The ablation system 60 includes an ablation catheter 10 and a coaxial guiding catheter 50. An ablating element 20 is disposed on the distal portion 16 of the ablation catheter 10. The guiding catheter 50 includes a handle 58 attached to the proximal end portion 54.

Figure 2A:
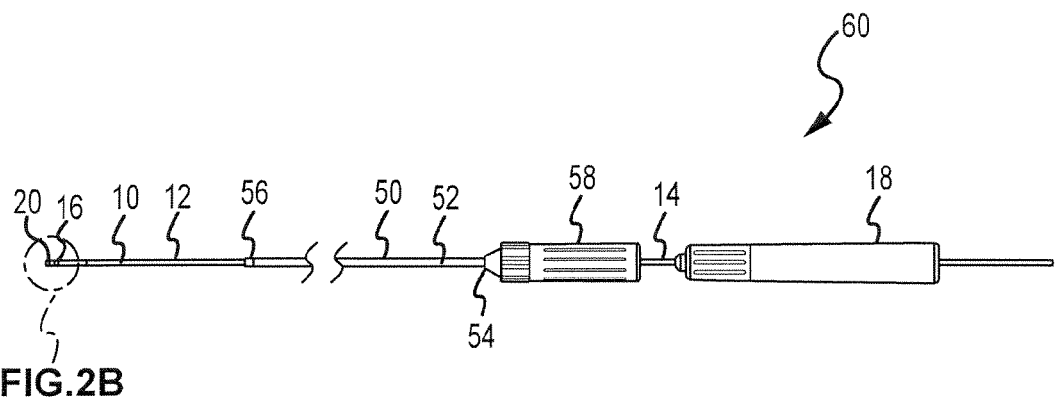
FIG. 2A is a top view of another embodiment of an ablation system according to the present invention having a guiding catheter and a coaxial ablation catheter.
Figure 2B:
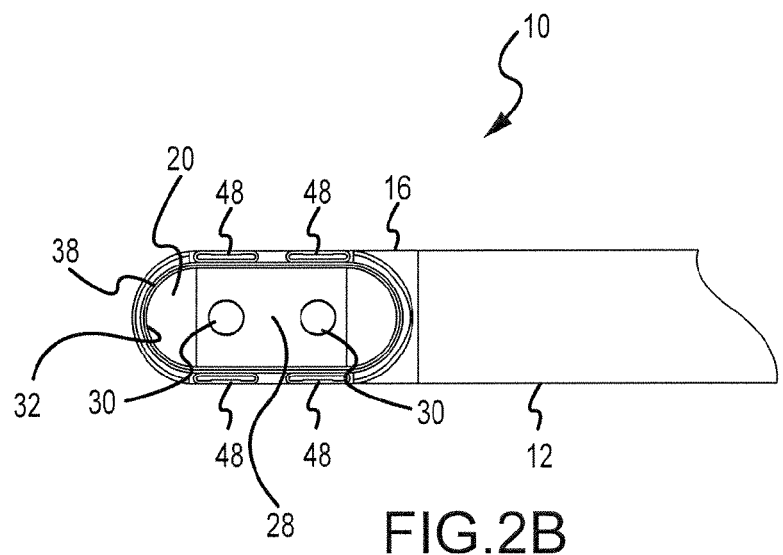
FIG. 2B depicts a top view of the distal portion of the ablation catheter depicted in FIG. 2A.
Figure 10:
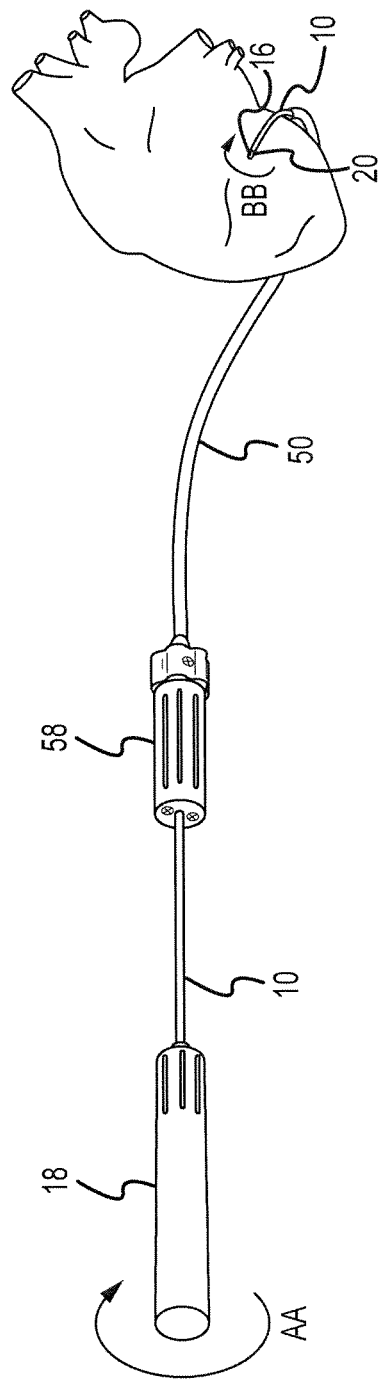
FIG. 10 is a simplified, perspective view depicting an ablation system contacting an epicardial surface as described herein.

Referring to FIGS. 1, 2A/B, 3, 4A/B, 5A/B, and 6-8, the guiding catheter 50 includes an elongate body 52 having a lumen 55 extending therethrough, a proximal end portion 54, a distal end 56 and a handle 58 connected to the proximal end portion 54. In one embodiment, a distal portion 62 of the guiding catheter 50 comprises a preformed member having a curved configuration, such as an arbitrary or complex shape, or the like, or as illustrated in FIG. 10, a partial hoop, hook or C-shape. In another embodiment, the guiding catheter 50 includes steering mechanisms or elements, such as resilient pull wires and anchor rings, making it steerable by an operator. That is, structure that permits the distal portion 62 to curve and/or deflect to access a desired target tissue location or ablation site.

The ablation catheter 10 slides axially within the lumen 55 of the guiding catheter 50 in coaxial relationship. The ablation catheter 10 includes an elongate body 12 having a lumen 15 extending therethrough, a proximal end 14 and a distal portion 16. A handle 18 mechanically couples to the proximal end 14 of the elongate body 12. The distal portion 16 includes one or more ablating elements 20. A single ablating element 20 (as depicted in the figures) or two or more ablating elements 20 can operatively couple to the distal portion 16 of the elongate body 12.

Figure 3:
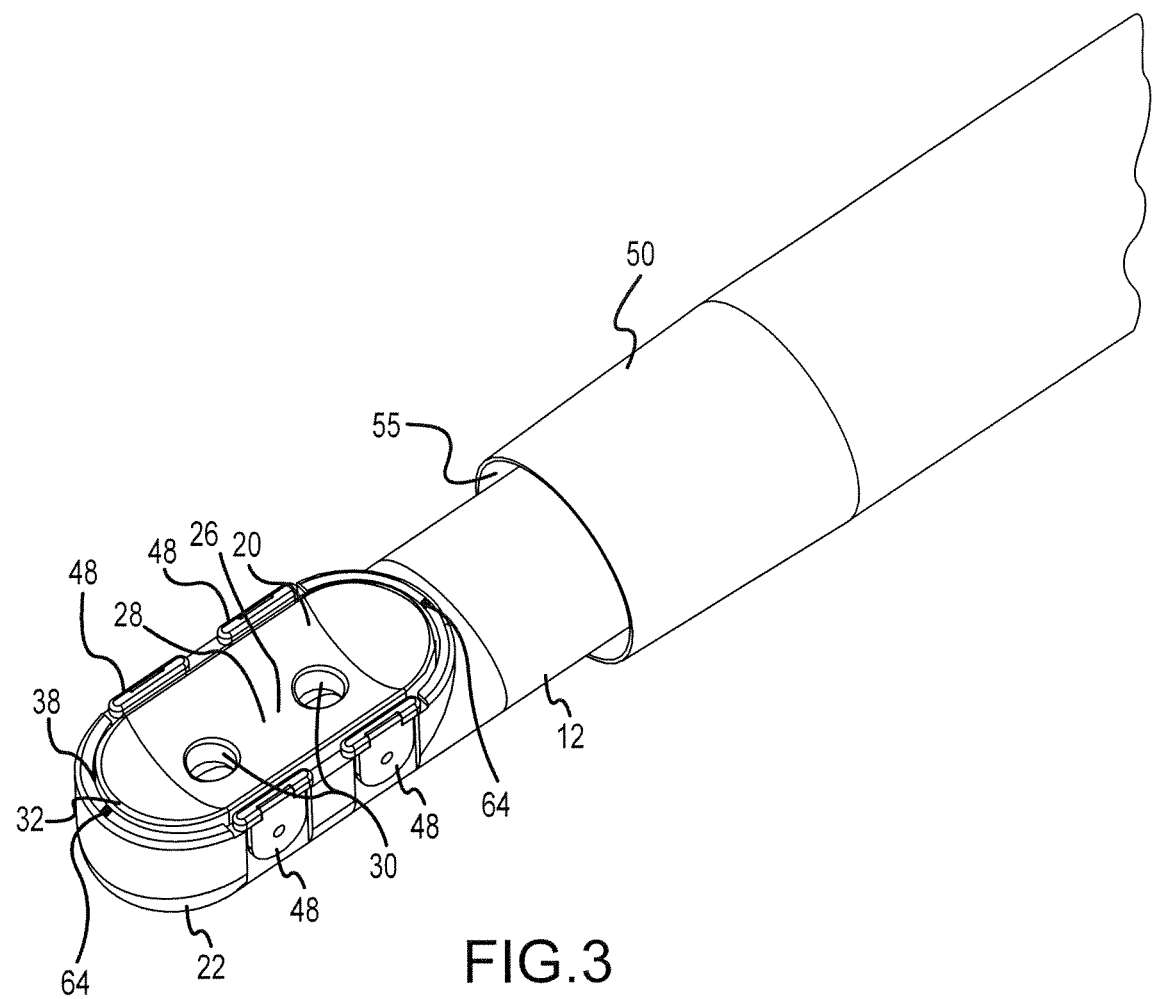
FIG. 3 illustrates a close-up perspective view of the distal portion of an ablation catheter in a coaxial relationship with a guiding catheter.

Referring to FIGS. 3 and 5B, for example, the ablating element 20 is mounted in a housing 22 that is affixed to the distal end of the elongate body 12. The ablating element 20 includes a first surface 24 disposed within the interior of the housing 22 and a second surface 26 opposite the first surface 24. The second surface 26 provides an interface between the ablating element 20 and the tissue. During use, the second surface 26 is oriented towards and positioned adjacent to a target tissue for ablation. The second surface 26 has a base portion 28 and a rim 32 that defines the perimeter or circumference of the ablating element 20. At least one port 30 extends through the ablating element 20 from the first surface 24 to the second surface 26. In one embodiment, the at least one port 30 extends through the base portion 28 of the second surface 26, but it is contemplated that the at least one port 30 may extend through any portion of the second surface 26 between the base portion 28 and the rim 32. The at least one port 30 is coupled to a source of varying pressure (not shown), for example a vacuum pump. Activation of the source of varying pressure results in a pressure differential between the ablating element 20 and the tissue, the second surface 26 defining a region of lower pressure compared to the ambient pressure, that draws the ablating element towards the tissue and stabilizes the device relative to the tissue.

In one embodiment, the second surface 26 has a curved or concave shape, such as the hemicapsule shape depicted in the figures. A hemicapsule shape is described as a cylinder capped with hemispheres that is divided in half along the axis of the cylinder. Other variations of the hemicapsule shape are also possible, for example, a hemisphere, a hemicylinder, and a hemi-ellipsoid, or any other configuration that provides for a volume of space that increases the effective surface area of the second surface 26. The concave shape allows the second surface 26 to conform to the contours of the target tissue. The concave shape also permits the ablating element 20 to be drawn towards the tissue when a vacuum is applied so that the ablating element 20 can be maintained in a stable position relative to the tissue. While various curved or concave shapes have been discussed herein, it is also contemplated that the second surface 26 may be flat.

In another embodiment, the ablating element 20 is a radiofrequency (RF) ablating element. The RF ablating element is a conductive metal having, in one embodiment, a concave surface as described above. The metal may be any conductive metal or a metal alloy consisting of one or more of gold, silver, platinum, iridium, titanium, tantalum, zirconium, vanadium, niobium, hafnium, aluminum, silicone, tin, chromium, molybdenum, tungsten, manganese, beryllium, cobalt, nickel, palladium, osmium, rhenium, technetium, rhodium, ruthenium, cadmium, zinc, germanium, antimony, bismuth, boron, scandium and metals of the lanthanide and actinide series, or any other biocompatible material. In some embodiments, it may be desirable to include a layer of biocompatible material covering the conductive metal. In another embodiment, the ablation catheter 10 may incorporate other types of ablating elements suitable for forming ablation lesions such as a microwave transmitter, a cryogenic element, an optical element, or an acoustic transducer, for example a high intensity focused ultrasound transducer.

In one embodiment, the ablating element 20 has a length of about 5 mm to about 10 mm and has a width of about 1 mm to about 5 mm. In another embodiment, the ablating element has a length of about 6 mm and a width of about 3.25 mm. In a further embodiment, the ablating element has a length of about 7 mm and a width of about 3.25 mm. It is to be understood that the ablating element 20 does not necessarily have a rectangular shape as the described dimensions may suggest, but may have the concave or hemispherical shapes discussed herein. Thus, the dimensions provided are merely exemplary and are not intended to be limiting.

As previously noted, the ablating element 20 includes at least one port 30 extending through the ablating element 20 from the first surface 24 to the second surface 26. The at least one port 30 is an opening or aperture that extends through the ablating element 20. The at least one port 30 is coupled to a source of varying pressure (not shown) so that a low pressure region can be established between the second surface 26 of the ablating element 20 and the target tissue. Two ports 30 are depicted in the embodiment shown in FIG. 3. In other embodiments, the ablating element 20 includes a single port 30 or more than two ports as would be appreciated by a person of skill in the art. The size of the ports 30 is selected to provide a region of relatively low pressure as between the ablating element 20 and the tissue, such as through the application of a vacuum, to maintain the ablating element 20 in a stable position relative to the tissue, and at the same time to reduce the risk that the tissue may be drawn into the ports 30, thus occluding or impeding the ports 30. The size and number of the ports 30 may be varied according to the application.

In one embodiment, the port 30 is circular, however, as a person of skill in the art appreciates, the shape of the one or more ports 30 can be designed and fabricated having diverse and/or differing shapes and cross-sectional areas, for example, having an oval, square, rectangular, slit, or any other regular or irregular shape, area, and cross-section. In another embodiment, the port 30 may be substantially circular with a plurality of narrow off-shoots or appendages extending radially outwardly to form a star-like configuration.

Referring to FIGS. 5A and 5B, the ports 30 couple to at least one suction lumen 36. The suction lumen 36 extends through the elongate body 12 and may be connected to a source of varying pressure (not shown), such as a vacuum source. The suction lumen 36 may be a tube or other channel. The suction lumen 36 may connect directly to the ports 30, or the suction lumen 36 may couple to a suction cavity 34 that connects to the ports 30. The suction cavity 34 can serve as a manifold to couple multiple ports 30 to the suction lumen 36. If the ablation catheter 10 includes more than one port 30, a separate suction lumen 36 may be coupled to each port 30, or a single suction lumen 36 may be coupled to each of the ports 30. The suction lumen 36 may be a separately-formed tube or lumen extending through the lumen 15 of the elongate body 12, or the suction lumen 36 may be integrally-formed within the lumen 15 of the elongate body 12. In use, when the vacuum source is activated, an area of low pressure relative to the ambient pressure is formed in the region of the ports 30 on the second surface 26, which draws the ablating element 20 towards the adjacent target tissue.

In another embodiment, the suction lumen 36 can be operated in a reverse flow manner. In this embodiment, the suction lumen 36 is coupled to a source of fluid, for example saline, and fluid is delivered through the suction lumen 36 and the ports 30 to expel or remove obstructions or debris. The suction lumen 36 may be interchangeably coupled to both a source of fluid and a source of varying pressure via a valve, or the suction lumen 36 may be manually coupled to either a source of fluid or a source of varying pressure to switch between a stabilizing mode and an irrigating mode.

Figure 9:
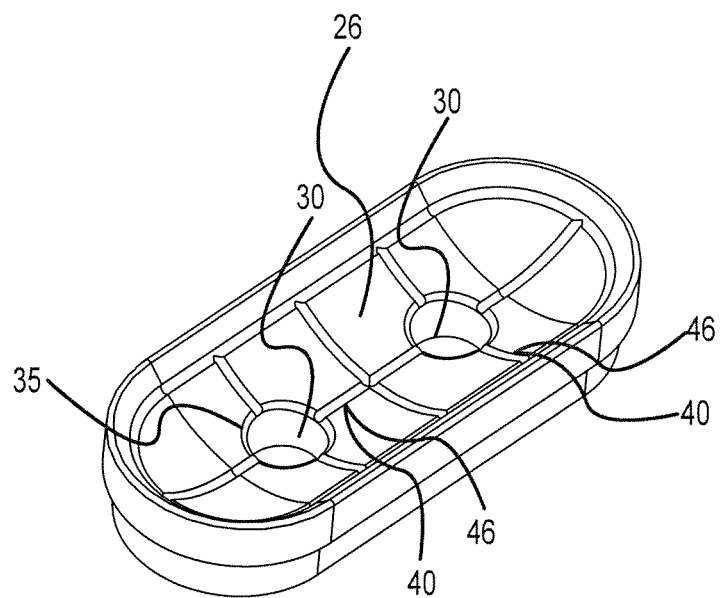
FIG. 9 is an enlarged perspective view of an ablating element having a textured surface.

Referring now to FIG. 9, in one embodiment, the ablating element 20 includes an anti-occlusion element 40 on the second surface 26 that prevents the tissue from being drawn into the ports 30 and occluding the ports 30 resulting in loss of tissue capture. In embodiments having two or more ports, occluding one port may result in loss of contact at the other ports. Thus, it is useful to provide a mechanism to reduce or eliminate the incidence of port occlusion. As shown in FIG. 9, the anti-occlusion element 40 may be a series of grooves 46 formed on the second surface 26 of the ablating element 20. The grooves 46 are depressions, textures or indentations formed or etched on the second surface 26 that communicate with the port 30. In other words, the grooves 46 connect to or join an outer edge 35 of the at least one port 30. In one embodiment, the anti-occlusion element 40 may include a series of grooves 46 expanding radially outwardly from the outer edge 35 of the port 30 to the rim 32. In another embodiment, the anti-occlusion element 40 may include a series of ridges or protuberances (not illustrated) on the second surface 26. The ridges or protuberances may be raised elements arranged in various patterns to give the second surface 26 texture or roughness.

In yet a further embodiment, the anti-occlusion element 40 may include a conductive mesh or screen (not shown) overlaying and adhered to at least a portion of the second surface 26. The conductive mesh or screen prevents tissue from being sucked into the port 30 and clogging or plugging the port 30. In one embodiment, the mesh or screen is thermally conductive and/or non-attenuating so that it does not interfere with the delivery of ablative energy during use—the ablative energy will transmit through the mesh or screen. In another embodiment, the conductive mesh or screen is made of a metallic material, such as a metallic wire, alloy or clad material, a conductive polymer material, a conductive composite material, or a conductive fibrous material. The conductive mesh or screen overlays and is affixed to the second surface 26 and may be electrically coupled to the ablating element 20. Alternatively, the mesh or screen may be made of an RF-transmissive (i.e., non-attenuating), non-conductive material such as a polymer. The mesh or screen may overlay the entire surface of the second surface 26 or a portion of the second surface 26 that includes the at least one port 30. A combination of anti-occlusion elements may also be used, for example, both ridges and a mesh or a screen.

In yet another embodiment, a button electrode is disposed on the second surface 26. The button electrode can be disposed on the base portion 28 of the second surface 26, or on any portion of the second surface 26 between the base portion 28 and the rim 32. The second surface 26 may or may not comprise a conductive material. In one embodiment, the second surface 26 is made of a conductive material, and the button electrode is surrounded by or embedded in an insulative material. In another embodiment, the rim 32 is made of a non-metallic, non-conductive and pliant material.

Referring again to FIGS. 3, 5A and 5B, in yet another embodiment, the ablation catheter 10 includes an irrigation channel 38 surrounding at least a portion of the rim 32 of the ablating element 20. In one embodiment, the irrigation channel 38 completely surrounds the rim 32. The irrigation channel 38 is a narrow passage or opening that permits a fluid to flow to the tissue in the vicinity of the ablating element 20. The fluid may be saline, hypertonic saline, water, refrigerant, or the like and may be used to cool the tissue and/or as a transmission medium for delivering energy, such as RF or ultrasonic energy, to the tissue. The irrigation channel 38 is in fluid communication with an irrigation lumen 42. The irrigation lumen 42 extends through the lumen 15 of the elongate body 12 and couples to a fluid source (not shown). In one embodiment, a distal end of the irrigation lumen 42 couples directly to the irrigation channel 38. In another embodiment, the irrigation lumen 42 couples to an irrigation inlet port 44 which couples to the irrigation channel 38. The source of varying pressure and the fluid source can be activated either independently or simultaneously without one interfering with or disrupting the other. Accordingly, control of the source of pressure overcomes any incoming irrigation fluid while maintaining suction stabilization relative to the target tissue.

The ablation catheters described and depicted herein are directional. In other words, successful ablation depends on proper orientation of the ablating element 20 relative to the target tissue. For example, when ablating epicardial tissue, the second surface 26 must be operatively oriented with respect to the target tissue (e.g., towards the cardiac myocytes forming the epicardium).

Figure 6:
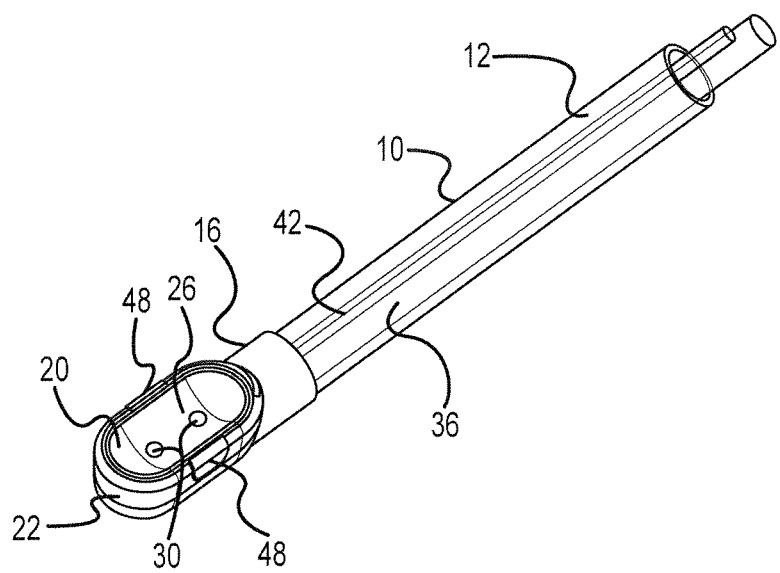
FIG. 6 illustrates a partial perspective view of an ablation catheter described herein.
Figure 7:
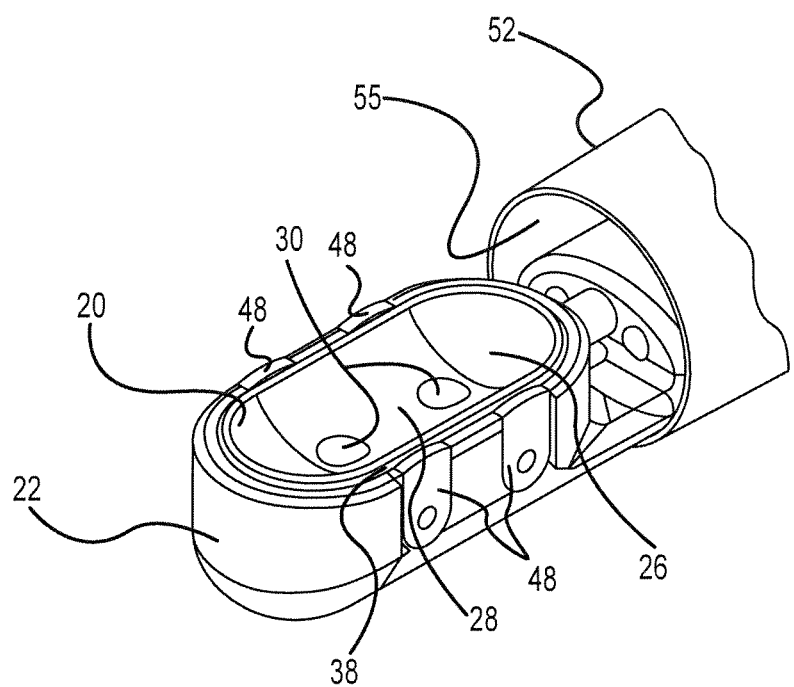
FIG. 7 depicts a partial perspective view of the distal portion of an ablation system described herein.
Figure 8:
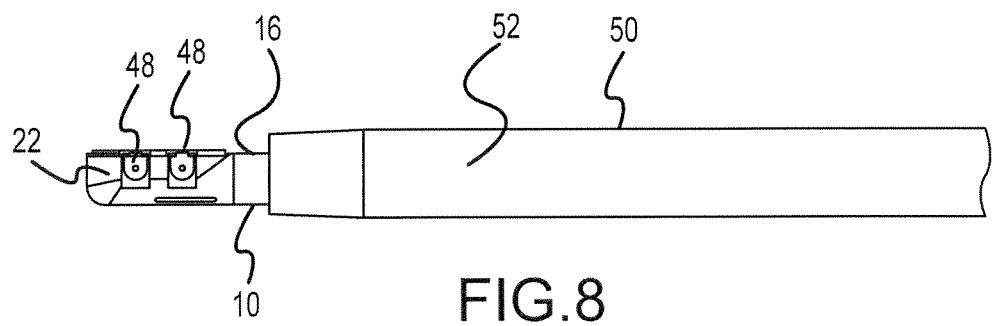
FIG. 8 is a side elevation view of an ablation system described herein.

In a further embodiment, to assist in orienting and locating, the ablation catheter 10 includes one or more electrodes 48 disposed on the distal portion 16 of the elongate body 12 (see FIG. 3, for example). The electrodes 48 may advantageously be used to orient the ablation catheter 10 to ensure that the second surface 26 of the ablating element 20 is facing or oriented towards the tissue desired to be ablated. In a particular configuration, the electrodes 48 may be unipolar or bipolar electrogram (EGM) electrodes adapted to measure electrical activity present on a surface of the tissue. For example, in one embodiment, a pair of bipolar electrodes 48 is disposed on an outer surface of the housing 22, the electrodes in the pair being disposed on opposite sides of the ablating element 20, as shown in FIG. 6, for example. In another embodiment, two pairs of bipolar electrodes 48 are used, as shown in FIG. 3, for example. The electrodes 48 are disposed on opposite sides of the ablating element 20 in a lateral direction generally perpendicular to a central axis of the elongate body 12 of the ablation catheter 10. Alternatively, or in addition to the foregoing, a bipolar pair of electrodes 48 may be disposed on opposite sides of the ablating element 20 in a lateral direction generally parallel to a central axis of the catheter body. In one embodiment, a side portion of the electrodes 48 (i.e., a portion that is exposed on the side of the housing 22, as shown in FIG. 3), is covered in a biocompatible material to prevent pacing and/or sensing of tissue that may contact the side portion of the electrodes 48. To ensure that the second surface 26 of the ablating element 20 is properly oriented towards the target tissue, the top portion of the electrodes 48 (i.e., the portion that is co-planar with the rim 32 of the second surface 26), emits and/or senses the pacing and/or sensing signals.

The electrodes 48 are coupled to an EGM-measurement circuit and a display or user interface for displaying EGM data. When the electrodes 48 are touching cardiac tissue, such as the epicardium, the electrodes 48 will sense an EGM signal. This will indicate to the user that the ablating element 20 is properly oriented. If the electrodes 48 do not sense an EGM signal, then the ablating element 20 is not facing cardiac tissue and must be re-oriented until an EGM signal is sensed. A signal can be activated for either or both states (i.e., electrodes coupled and not coupled to cardiac tissue) to alert the operator of a current state via a variety of modalities such as acoustic, visual, haptic or vibratory and the like.

In another embodiment, the electrodes 48 are used for diagnostic purposes, for example, to confirm that an effective lesion has been created. In this embodiment, the electrodes 48 are coupled to an impedance-measuring circuit. An ablation lesion is non-conductive scar tissue; thus, the lesion blocks electrical signals. Because impedance measures resistance, the effectiveness of an ablation lesion can be determined based on impedance measurements. Impedance can be measured before, during or after applying ablative energy to the tissue. If an effective lesion has been created, the impedance will be higher after ablation compared to pre-ablation impedance measurements. Also, impedance can be used to identify a discontinuity in an ablation lesion (i.e., the impedance will be lower near the discontinuity).

In a further embodiment, a pair of electrodes 48 is used confirm the completeness of a lesion in a pacing and sensing mode. In this embodiment, a pair of electrodes 48 is positioned on opposite sides of the ablating element 20. A first electrode of the pair of electrodes 48 sends a pacing signal. The second electrode senses or detects the pacing signal only if the lesion is incomplete. Once an effective lesion is made, the second electrode will no longer detect the pacing signal. In this embodiment, the electrodes 48 are connected to a pulse-generator and monitor as is known in the art. In an alternative embodiment, both of the electrodes 48 may be sensing electrodes with both electrodes sensing normal activity. When only one of the electrodes senses the activity an effective lesion has been created.

It is further contemplated that the rim 32 of the ablating element 20 operates as a pacing and/or sensing electrode. During use, the rim 32 of the ablating element 20 contacts the target tissue. Thus, the ablating element 20 can alternate or cycle between an ablating mode and a pacing and/or sensing mode. In this embodiment, the ablating element 20 is coupled to both an RF generator and a pulse-generator. It may be further desirable to include a suitable filtering and/or shielding mechanism when coupling the ablating element 20 to both a high power, high frequency RF generator and low power, low frequency pacing and sensing circuitry. Because of the relative difference in size between the ablating element 20 and the electrodes 48, suitable adjustments may need to be made to the pacing parameters. The ablating element 20 can be either unipolar or bipolar. In a bipolar configuration, the ablating element 20 operates with one or more of the electrodes 48 disposed on the housing 22. In an alternative embodiment, a ring electrode (not shown) is disposed on a distal end of the housing 22. When the ablating element 20 serves as a single conductor for both the high power, high frequency RF generator In another embodiment, the ablation device 10 includes one or more temperature sensors 64, such as thermistors or thermocouples, disposed on the distal portion 16 of the elongate body 12 (see FIG. 3). The one or more temperature sensors are positioned to measure the temperature of the ablating element 20, the fluid that flows through the irrigation channel 38 to the tissue, and/or the tissue. In one embodiment, temperature sensors 64 are positioned distally and/or proximally of the ablating element 20 as shown in FIG. 3. Temperature readings from the one or more temperature sensors 64 may be output and presented as advisory data to a practitioner (analogous to the above relating to the state of the electrode(s)). For example, temperature readings may be presented via a display (e.g., a color, number, or symbol), a tone (e.g., an audible alarm), and/or haptic or vibratory feedback. This allows the practitioner to adjust the rate at which energy is delivered by the ablating element 20 and/or the rate at which a fluid is delivered through the irrigation lumen 42 in order to maintain a particular temperature or temperature range at the tissue.

Referring to FIGS. 2A, 3 and 10, the elongate body 12 of the ablation catheter 10 is slideably disposed through the lumen 55 of the guiding catheter 50 in a coaxial configuration.

Figure 13:
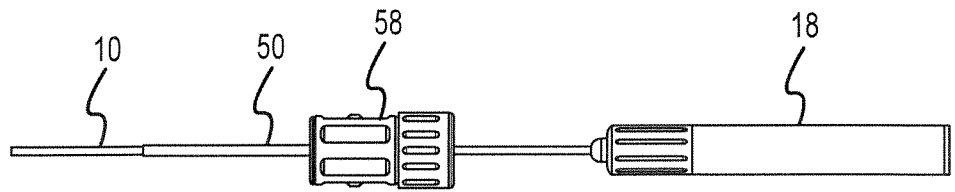
FIG. 13 is a side view depicting another handle design for ablation systems described herein.
Figure 14:
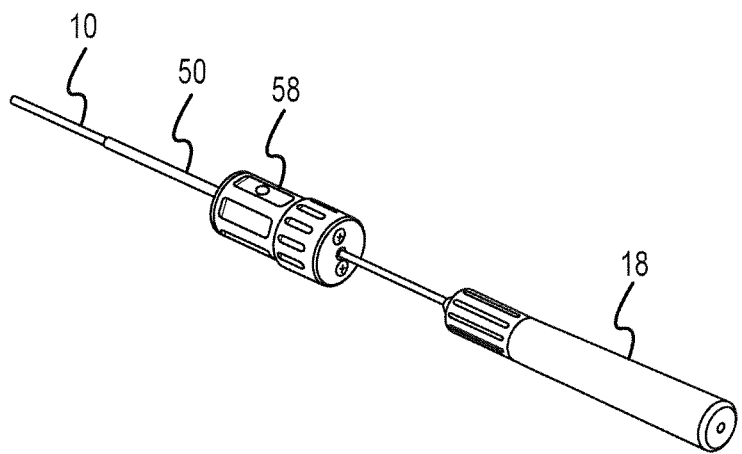
FIG. 14 is a perspective view of the handle design depicted in FIG. 13.

In one embodiment, both the ablation catheter 10 and the guiding catheter 50 are steerable and/or deflectable. In this embodiment, the ablation catheter 10 and the guiding catheter 50 include one or more steering wires or pull wires (not shown) within the elongate bodies 12, 52 of the ablation catheter 10 and the guiding catheter 50, respectively. The handle 18 of the ablation catheter 10 and the handle 58 of the guiding catheter 50 include actuators for steering and/or deflecting the catheters. In another embodiment, the handles 18, 58 are different in size and/or shape so that a practitioner can easily distinguish one from the other during a medical procedure. In a further embodiment, the handles or user interfaces 18, 58 are tactilely unique, meaning they each have a different feel or texture relative to the other. For example, one handle may have a soft or spongy surface while the other handle has a hard or stiff surface. Alternatively, one handle may have a smooth surface compared to a rough or textured surface on the other handle. It is advantageous to provide an ablation system in which the handles 18, 58 on the ablation catheter 10 and the guiding catheter 50 are different in size, shape and/or tactility to permit a practitioner to easily and quickly identify and distinguish the handle for controlling the ablation catheter 10 versus the handle for controlling the guiding catheter 50 during a medical procedure. As shown in FIGS. 13 and 14, in one embodiment, the handle 18 attached to the ablation catheter 10 is longer and more narrow than the handle 58 attached to the guiding catheter 50.

Referring to FIG. 10, the ablation catheter 10 is configured in a coaxial relationship with both the handle 58 of the guiding catheter 50 and the lumen 55 of the guiding catheter 50. The handle 58 on the guiding catheter 50 may be manipulated to steer and/or deflect the guiding catheter 50 to direct the distal end 56 to a location near a tissue to be ablated. The handle 18 on the ablation catheter 10 may also be manipulated to steer and/or deflect the ablation catheter 10. The guiding catheter 50 provides a pathway for delivering the distal portion 16 of the ablation catheter 10 to the tissue site for ablation. The guiding catheter 50 also advantageously constrains the ablation catheter 10 within the lumen 55 of the guiding catheter so that the ablating element 20 can be properly oriented against the tissue to be ablated. More specifically, the distal portion 16 of the ablation catheter 10 is advanced distally until the distal portion 16 extends beyond the distal end 56 of the guiding catheter 50. In one embodiment, the distal portion 16 of the ablation catheter 10 is advanced about 5 cm to about 15 cm beyond the distal end 56 of the guiding catheter 50. The handle 18 of the ablation catheter 10 can then be rotated axially as shown by the arrow AA depicted in FIG. 10. Rotating the handle 18 causes the distal portion 16 of the ablation catheter 10 to also rotate axially as shown by the arrow BB. Because it is constrained within the guiding catheter 50, the distal portion 16 of the ablating catheter 10 spins or rotates within the guiding catheter 50, whereas were the distal portion 16 not constrained within the guiding catheter 50, the distal portion 16 would bend and deflect in a random and uncontrollable fashion. Thus, not only does the guiding catheter 50 provide means for guiding the ablation catheter 10 to the desired ablation site, the guiding catheter 50 also advantageously assists in properly orienting the second surface 26 of the ablating element 20 in relation to the tissue to be ablated.

Figure 11:
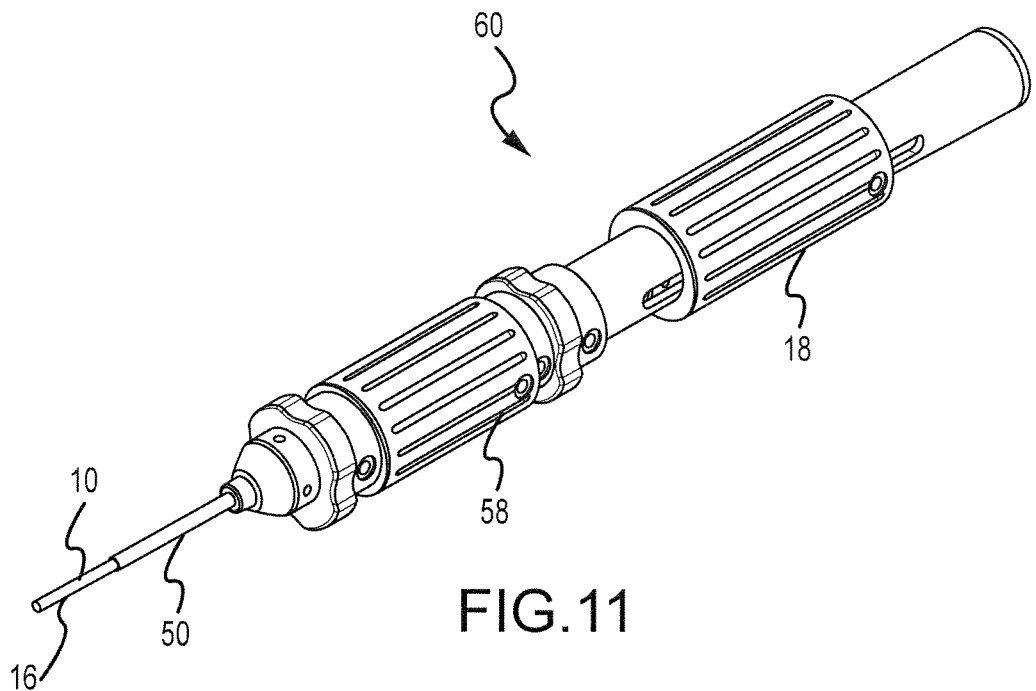
FIG. 11 illustrates a perspective view of a handle design for use with the present ablation systems.
Figure 12:
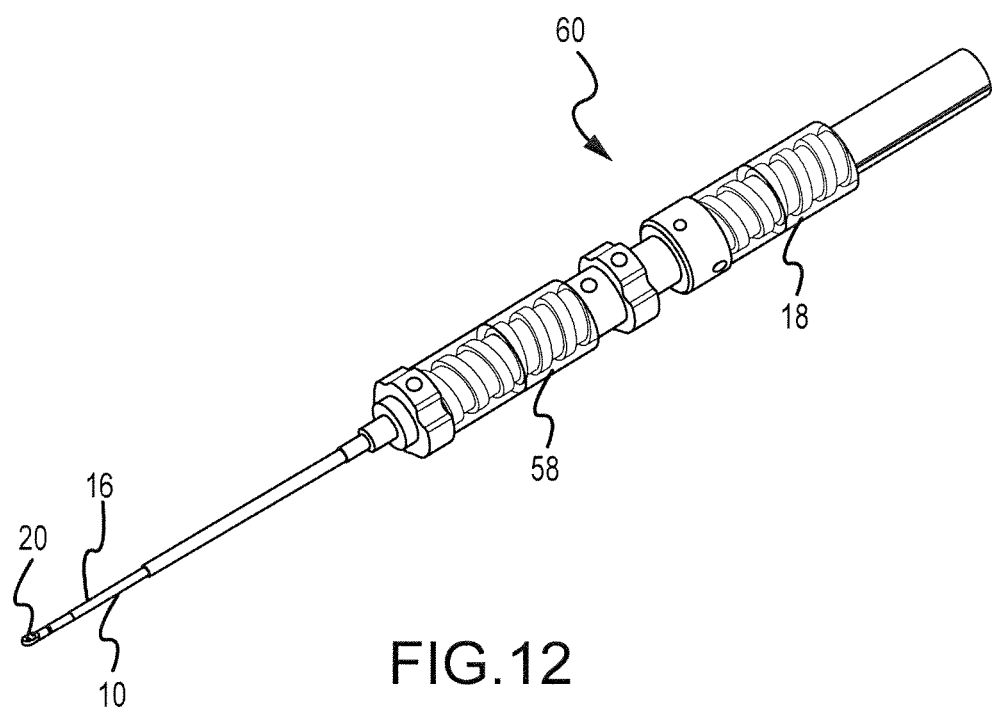
FIG. 12 is a fragmentary view illustrating exemplary internal portions of the handle depicted in FIG. 11.

FIGS. 11 and 12 depict the dual-handle configuration in a single system. The ablation system 60 includes a first handle 58 for controlling the guiding catheter 58 and a second handle 18 for controlling the ablation catheter 10. The ablation catheter handle 18 is adapted to move back and forth in a distal and proximal direction to advance and withdrawal the distal portion 16 of the ablation catheter 10 through the guiding catheter 50. The handles 58, 18 are also rotatable axially relative to a longitudinal axis of the catheter bodies.

Figure 15:
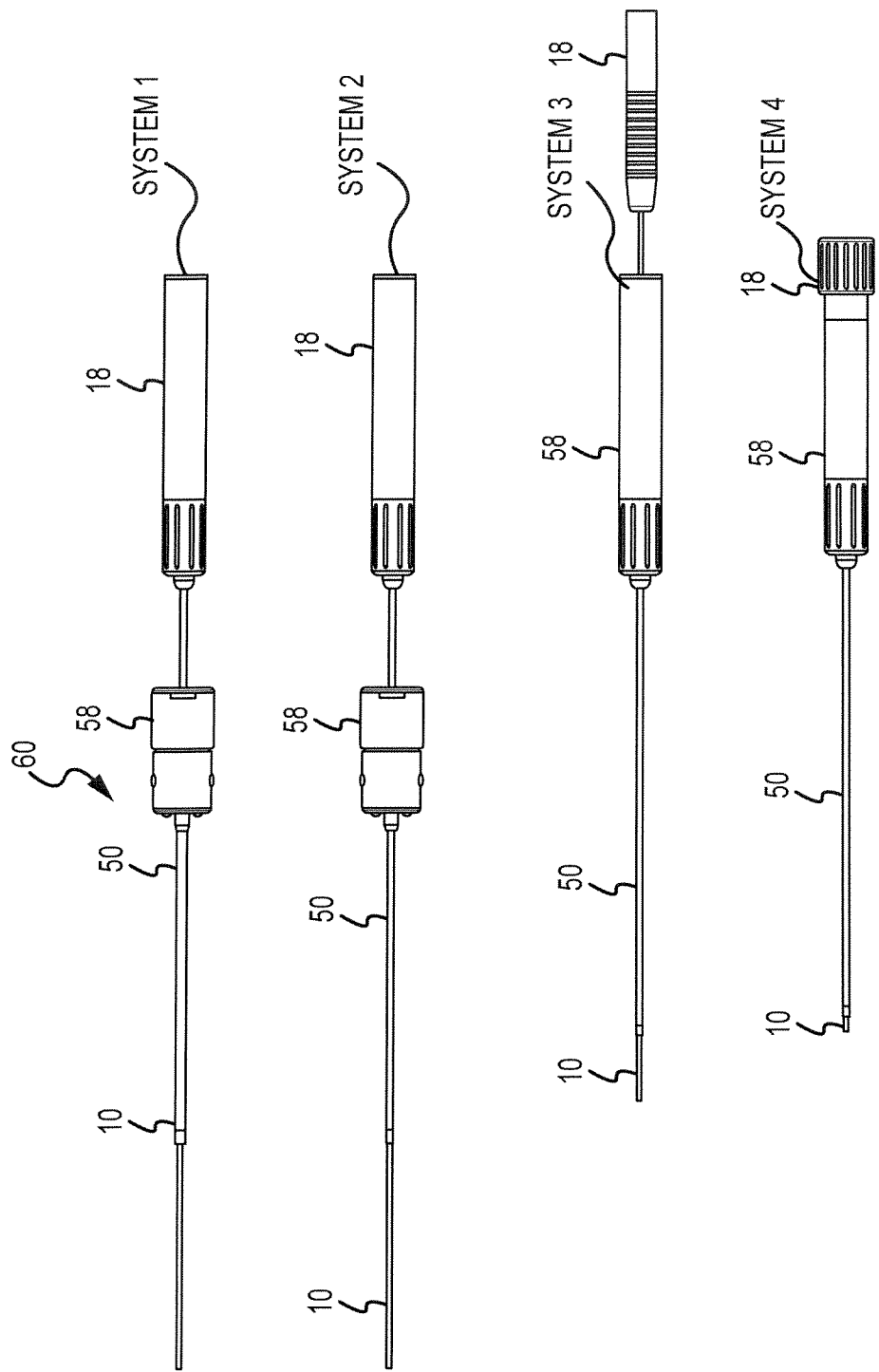
FIG. 15 illustrates various ablation system configurations as described herein.

Referring to FIG. 15, various combinations of handle configurations can be used to provide different levels of control. In addition, the ablation catheter 10 can be made so that it is not removable or separable from the guiding catheter 50. In System 1, the handle 58 for the guiding catheter 50 includes an actuator for deflecting the guiding catheter 50. The handle 18 of the ablation catheter 10 is axially rotatable relative a longitudinal axis of the elongate catheter body 12 to effect axial rotation of the distal portion 16 of the ablation catheter 10. The ablation catheter handle 18 can be advanced distally to extend the distal portion 16 of the ablation catheter 10 up to about 35 cm beyond the distal end 56 of the guiding catheter 50. The guiding catheter has an inner diameter of about 4-5 mm. The ablation catheter 10 can be removed from the lumen 55 of the guiding catheter 50. System 2 is similar to System 1, however the guiding catheter 50 has an inner diameter of about 3-4 mm, and the ablation catheter 10 is not removable from the lumen 55 of the guiding catheter 50.

In System 3, the handle 18 for the ablation catheter 10 can be advanced distally to extend the distal portion 16 of the ablation catheter 10 up to about 5 cm. The ablation catheter handle 18 is also axially rotatable relative a longitudinal axis of the elongate catheter body 12 to effect axial rotation of the distal portion 16 of the ablation catheter 10. In System 4, the ablation catheter handle 18 is axially rotatable, but cannot be advanced distally to extend the distal portion 16 of the ablation catheter 10 beyond the distal end 56 of the guiding catheter 50. In both Systems 3 and 4, the guiding catheter has an inner diameter of about 3-5 mm, and the ablation catheter 10 can be removed from the lumen 55 of the guiding catheter 50. The ablation systems described herein may incorporate the handle designs and steering mechanisms used in known steerable introducer systems such as the Agilis™ NxT Steerable Introducer and/or steerable catheter systems such as the Livewire TC™ Ablation Catheter, currently distributed by St. Jude Medical, Atrial Fibrillation Division, Inc. of St. Paul, Minn.

Methods of ablating tissue will now be described. In one embodiment, the method includes providing a guiding catheter 50 and providing an ablation catheter 10 slidably disposed within a lumen 55 of the guiding catheter 50. The guiding catheter 50 includes an elongate guiding catheter body 52 defining a lumen 55 extending therethrough, a distal end 56, a proximal end portion 54 and a handle 58 mechanically coupled to the proximal end portion 54. The ablation catheter 10 includes some or all of the elements previously described herein. For example, the ablation catheter 10 includes an elongate ablation catheter body 12 having a proximal end 14, a handle 18 mechanically coupled to the proximal end 14, and a distal portion 16 having means for ablating a target tissue. The ablation catheter 10 further includes components to orient the distal portion 16 of the ablation catheter with respect to a target tissue, components to maintain the distal portion 16 of the ablation catheter in a stable position relative to a target tissue, and components to irrigate the target tissue. In one embodiment, the ablation catheter 10 and the guiding catheter 50 are configured to permit the ablation catheter 10 to be inserted and removed from the guiding catheter 50. In another embodiment, the ablation catheter 10 and guiding catheter 50 are configured such that the ablation catheter 10 is not removable or separable from the guiding catheter 50.

The methods described herein include, in one embodiment, inserting the guiding catheter 50 into a body cavity and advancing the guiding catheter 50 to a location near an epicardial ablation target site. The guiding catheter 50 may be inserted via known methods, including minimally-invasive methods. In one embodiment, the guiding catheter 50 is inserted into the pericardial space via a percutaneous subxiphoid approach. The ablation catheter 10 is slideably disposed within the lumen 55 of the guiding catheter 50 and advanced until the distal portion 16 of the ablation catheter 10 exits the distal end 56 of the guiding catheter 50. In one embodiment, the distal portion 16 of the ablation catheter 10 is advanced about 5 cm to about 15 cm beyond the distal end 56 of the guiding catheter 50. Alternatively, the ablation catheter 10 and the guiding catheter 50 may be a single device such that the ablation catheter 10 is slidably disposed within the guiding catheter 50, but is not separable from the guiding catheter. In this embodiment, the guiding catheter 50 and ablation catheter 10 are inserted into a body cavity simultaneously and the distal portion 16 of the ablation catheter 10 may then be advanced or extended beyond the distal end 56 of the guiding catheter 50.

The ablating element 20 is then oriented to place the second surface 26 in contact with or facing the target tissue, for example an epicardial tissue. In one embodiment, the ablation catheter handle 18 is rotated or otherwise manipulated to cause axial rotation of the distal portion 16 of the ablation catheter 10. In other words, the distal portion 16 of the ablation catheter 10 rotates axially about a longitudinal axis of the ablation catheter body 12. EGM activity is sensed using the one or more electrodes 48 that are disposed on the distal portion 16 of the ablation device 10 near the ablating element 20. When an EGM signal is sensed, the second surface of the ablating element is facing or contacting the epicardium. Thus, the practitioner continues to move or rotate the ablation catheter handle until an EGM signal is sensed, and optionally receives a signal indicating the orientation of the electrodes 48 and thus, the ablating element 20.

Once the practitioner is confident that the second surface 26 is properly oriented in relation to the target tissue, a source of varying pressure, for example a vacuum pump, is activated to establish a region of low pressure near the second surface 26 of the ablating element 20 via the ports 30. The region of low pressure maintains the ablating element 20 in a stable position and/or minimizes movement of the ablating element 20 relative to the target tissue. As noted previously, more than one ablating element 20 can couple to the distal portion 16 of the ablation catheter 10 and in that case one or more discrete low pressure regions can be implemented.

The methods further include delivering a fluid to the target tissue. The fluid, such as saline, hypertonic saline, water, refrigerant, or the like, flows through the irrigation lumen to the irrigation channel surrounding the ablating element to irrigate or cool the tissue. In one embodiment, the temperature of the tissue is monitored via one or more temperature sensors 64. The ablating element is then activated via a source of ablative energy to ablate the target tissue. In a further embodiment, the ablation catheter 10 is slowly withdrawn back through the guiding catheter 50 in a proximal direction while ablative energy is applied to the tissue to create a linear lesion. The vacuum pump may need to be temporarily shut-off or reduced to effect movement of the ablation catheter.

It is contemplated that, in one embodiment, the fluid does not enter the low pressure area where the tissue is stabilized. In other words, the vacuum pressure is sufficiently low to maintain a boundary of contact between the tissue being ablated and the fluid such that the fluid does not enter the ports 30 or the suction lumen 36.

After ablating the tissue, the completeness of the ablation lesion can be confirmed using the one or more electrodes 48. For example, in one embodiment, the electrodes 48 measure an impedance, as previously described herein. In a second embodiment, a first electrode may send a pacing signal across the lesion to determine if the lesion is complete. If a second electrode positioned on the opposite side of the ablating element 20 relative to the first electrode does not detect the pacing signal, or the signal is received relatively later than a pacing signal sent and received previously, the lesion can be considered relatively complete and free of ion-conducting inter-lesion gaps. Alternatively, the electrodes 48 may be used to measure impedance of the tissue between the electrodes 48 compared to a pre-ablation measurement.

EXAMPLE

The following example of methods of use is provided as additional disclosure although the specifics should be generally appreciated by those of skill in the art to which this disclosure pertains.

A method of ablating epicardial tissue includes providing a guiding catheter, the guiding catheter comprising a body and a continuous lumen extending through the body, a distal end, a proximal portion, and a first handle coupled to the proximal end, and providing an ablation catheter slideably disposed within the lumen of the guiding catheter. The ablation catheter includes an elongate body defining a lumen therethrough, a proximal end, a second handle coupled to the proximal end, a distal portion, and at least one ablating element coupled to the distal portion. The at least one ablating element includes a first surface and a second surface, and the second surface includes a base portion, at least one port and a rim. The ablation catheter further includes at least one cardiac electrode coupled to the distal portion of the elongate body, a suction lumen coupled to the at least one port at a distal end thereof and a source of varying pressure at a proximal end thereof. Additionally, the ablation catheter includes an irrigation channel surrounding at least a portion of the rim, and an irrigation lumen fluidly coupled to the irrigation channel at a distal end thereof and a source of irrigation fluid at a proximal end thereof.

The method further includes inserting the guiding catheter and the ablation catheter into a body cavity, advancing the guiding catheter and the ablation catheter to a location near an epicardial tissue, and advancing the ablation catheter through the guiding catheter until the ablating element exits the distal end of the guiding catheter. The step of inserting a guiding catheter and the ablation catheter into a body cavity may include inserting the guiding catheter into the pericardial space via a percutaneous subxiphoid approach. The ablating element is oriented to place the second surface in contact with or facing an epicardial tissue, and the source of varying pressure is activated to maintain the ablating element in a stable position relative to the tissue, or minimize relative movement of the ablating element relative to the tissue. A fluid is delivered through the irrigation lumen and the irrigation channel to irrigate the tissue, and the ablating element is activated to ablate the tissue. To orient the ablating element in relation to the tissue, the second handle is manipulated to cause axial rotation of the distal portion of the ablation catheter relative to a longitudinal axis of the elongate ablation catheter body, and the at least one pair of electrodes sense electrical activity on the tissue to indicate when the ablating element is oriented towards the epicardial tissue. The at least one pair of electrodes may measure an impedance after ablating the tissue to confirm that an effective lesion has been created.

The recitation of one or more embodiments discussed or described herein does not imply that other embodiments are not useful and is not intended to exclude other embodiments from the scope of the invention and no disclaimer of other embodiments should be inferred from the discussion of a certain embodiment or a figure showing a certain embodiment.

Although multiple embodiments have been described above with a certain degree of particularity, those skilled in the art could make numerous alterations to the disclosed embodiments without departing from the teaching of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the disclosure and do not create limitations, particularly as to the position, orientation, or use of the subject matter herein described, depicted and claimed. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the teaching of this disclosure as defined in the appended claims.

What is claimed is:

1. A device for ablating tissue, comprising:
   an elongate body defining a lumen therethrough, the elongate body having a proximal end and a distal portion;
   at least one ablating element coupled to the distal portion of the elongate body having a first surface and a second surface, the second surface having a base portion, at least one port and a rim, wherein the rim defines an edge perimeter of the ablating element;
   at least one cardiac electrode coupled to the distal portion of the elongate body;
   a suction lumen coupled to the at least one port at a distal end thereof and a source of varying pressure at a proximal end thereof;
   an irrigation channel surrounding at least a portion of the rim; and
   an irrigation lumen fluidly coupled to the irrigation channel at a distal end thereof and a source of irrigation fluid at a proximal end thereof.

2. The device according to claim 1, wherein the at least one ablating element is a radiofrequency (RF) electrode.

3. The device according to claim 1, wherein the second surface is adapted to be oriented opposite a target tissue, and wherein the second surface comprises a concave shape.

4. The device according to claim 1, wherein the at least one ablating element further comprises an anti-occlusion element disposed at least one of on or near the second surface in communication with the at least one port.

5. The device according to claim 4, wherein the anti-occlusion element comprises at least one of a series of ridges, a series of grooves and a series of protuberances.

6. The device according to claim 4, wherein the anti-occlusion element comprises at least one of a conductive mesh and a conductive screen.

7. The device according to claim 1, wherein the at least one port comprises a circular configuration and wherein the second surface comprises a series of grooves extending radially outwardly from the at least one port.

8. The device according to claim 1, wherein the at least one port comprises two ports.

9. The device according to claim 1, wherein the device further comprises one or more steering wires extending through the elongate body.

10. The device according to claim 1, further comprising at least one temperature sensor coupled to a portion of the distal portion.

11. The device according to claim 1, further comprising an outer guiding sheath having a body shorter than the elongate body, a proximal handle, and a continuous lumen through said body and said proximal handle, said continuous lumen configured to slideably receive the elongate body therethrough while permitting mutual axial and radial motion of said elongate body and said body.

12. The device according to claim 11, wherein the outer guiding sheath further comprises means for steering at least a distal portion of said body.

13. An ablation tip for a medical device, comprising:
    a housing;
    a radiofrequency (RF) ablating element disposed within the housing, the RF ablating element comprising a first surface and a second surface having a base portion, at least one port and a rim, wherein the rim defines an edge perimeter of the ablating element, and the ablating element comprises an electrode;
    at least one pair of electrodes disposed along an outer surface of the housing on opposite sides of the RF ablating element;
    a suction cavity adjacent the first surface of the ablating element, the suction cavity being connectable to a suction lumen;
    an irrigation channel surrounding at least a portion of the rim; and
    an irrigation inlet port in fluid communication with the irrigation channel and being connectable to an irrigation inlet lumen.

14. The ablation tip according to claim 13, wherein the RF ablating element further comprises at least one anti-occlusion feature disposed at least one of on or near the at least one suction port, the anti-occlusion feature selected from at least one of: at least one ridge, at least one groove, a plurality of protuberances, a mesh, and a screen.

15. The ablation tip according to claim 13, further comprising at least one temperature sensor coupled to an outer surface of the housing.

16. The ablation tip according to claim 13, wherein the at least one port comprises two ports.

17. A device for ablating tissue, comprising:
    a guiding catheter having an elongate guiding catheter body, a first handle at a proximal end thereof, and a continuous lumen through the body and the first handle;
    an ablation catheter disposed within the continuous lumen permitting mutual axial and longitudinal movement of the guiding catheter and the ablation catheter, the ablation catheter comprising
      an elongate ablation catheter body defining a lumen therethrough, the elongate ablation catheter body having a proximal end and a distal portion;
      a second handle at the proximal end of the elongate ablation catheter body;
      at least one ablating element coupled to the distal portion of the elongate ablation catheter body, the at least one ablating element comprising a first surface and a second surface, the second surface having a base portion, at least one port and a rim, wherein the rim defines an edge perimeter of the ablating element;

at least one pair of electrodes disposed on opposite sides of the at least one ablating element, a suction lumen coupled to the at least one suction port and to a remote source of varying pressure disposed distally relative to the second handle;

an irrigation channel surrounding at least a portion of the rim and fluidly coupled to a remote source of irrigation fluid;

wherein controlled movement of the second handle allows the distal portion of the ablation catheter to rotate axially and displace longitudinally thereby placing the second surface of the ablating element in operative contact with a volume of target tissue.

18. The device according to claim 17, wherein the guiding catheter includes one or more components to translate a movement of the first handle into a deflection of the distal end of the guiding catheter.

19. The device according to claim 17, wherein the first handle and the second handle are fabricated with at least one of: a differing material, a differing geometry, a differing surface feature, and a differing topography thereby rendering the first handle and the second handle tactilely distinct from each other.

20. The device according to claim 17, wherein the at least one ablating element is a radiofrequency ablating element.

21. The device according to claim 17, wherein the ablation catheter further comprises at least one temperature sensor coupled to the distal portion.

\* \* \* \* \*